(12) United States Patent
Burkhardt et al.

(10) Patent No.: US 11,160,666 B2
(45) Date of Patent: Nov. 2, 2021

(54) LATERALLY INSERTABLE INTERVERTEBRAL SPINAL IMPLANT

(71) Applicant: GLOBUS MEDICAL, INC., Audubon, PA (US)

(72) Inventors: Alex Burkhardt, Akron, PA (US); Jenna Israel, Philadelphia, PA (US); Adam Friedrich, Cinnaminson, NJ (US)

(73) Assignee: Globus Medical, Inc., Audubon, PA (US)

( * ) Notice: Subject to any disclaimer, the term of this patent is extended or adjusted under 35 U.S.C. 154(b) by 124 days.

(21) Appl. No.: 16/515,780

(22) Filed: Jul. 18, 2019

(65) Prior Publication Data

US 2019/0336304 A1    Nov. 7, 2019

Related U.S. Application Data

(60) Continuation-in-part of application No. 16/205,892, filed on Nov. 30, 2018, now Pat. No. 10,925,750, (Continued)

(51) Int. Cl.
*A61F 2/44* (2006.01)
*A61F 2/30* (2006.01)
*A61F 2/28* (2006.01)

(52) U.S. Cl.
CPC ........ *A61F 2/4455* (2013.01); *A61F 2/30767* (2013.01); *A61F 2/442* (2013.01); (Continued)

(58) Field of Classification Search
CPC .......... A61F 2/44; A61F 2/442; A61F 2/4455; A61F 2/446; A61F 2/4465; A61F 2/447; A61F 2002/4475
See application file for complete search history.

(56) References Cited

U.S. PATENT DOCUMENTS

| 1,673,630 A | 6/1928 | Madge |
| 4,349,921 A | 9/1982 | Kuntz |

(Continued)

FOREIGN PATENT DOCUMENTS

| FR | 2727003 A1 | 5/1996 |
| JP | 2011502708 A | 1/2011 |

(Continued)

OTHER PUBLICATIONS

U.S. Appl. No. 60/777,663, filed Feb. 27, 2006, Messerli.
(Continued)

*Primary Examiner* — Eric S Gibson

(57) ABSTRACT

An intervertebral implant for implantation in an intervertebral space between vertebrae. The implant includes a body having a front end, a rear end and a pair of spaced apart first and second side walls extending between the front and rear ends. The front and rear ends extend in a transverse direction and a central axis of the body extends from the rear end to the front end. The rear end defines a first fastener hole having a first central axis and a second fastener hole having a second central axis. The first and second central axes extend parallel to one another at an acute angle relative to the body central axis in the transverse direction.

7 Claims, 7 Drawing Sheets

Related U.S. Application Data which is a continuation of application No. 15/954,655, filed on Apr. 17, 2018, now Pat. No. 10,179,053, which is a division of application No. 14/509,634, filed on Oct. 8, 2014, now Pat. No. 9,968,461, which is a continuation-in-part of application No. 14/278,898, filed on May 15, 2014, now Pat. No. 9,545,320.

(52) U.S. Cl.
CPC ...... *A61F 2/447* (2013.01); *A61F 2002/2835* (2013.01); *A61F 2002/302* (2013.01); *A61F 2002/3008* (2013.01); *A61F 2002/30014* (2013.01); *A61F 2002/3039* (2013.01); *A61F 2002/30187* (2013.01); *A61F 2002/30202* (2013.01); *A61F 2002/30322* (2013.01); *A61F 2002/30324* (2013.01); *A61F 2002/30387* (2013.01); *A61F 2002/30433* (2013.01); *A61F 2002/30482* (2013.01); *A61F 2002/30487* (2013.01); *A61F 2002/30571* (2013.01); *A61F 2002/30578* (2013.01); *A61F 2002/30593* (2013.01); *A61F 2002/30607* (2013.01); *A61F 2002/30616* (2013.01); *A61F 2002/30622* (2013.01); *A61F 2002/30787* (2013.01); *A61F 2002/30822* (2013.01); *A61F 2002/30823* (2013.01); *A61F 2002/30828* (2013.01); *A61F 2002/30843* (2013.01); *A61F 2002/30904* (2013.01); *A61F 2310/00011* (2013.01); *A61F 2310/00023* (2013.01); *A61F 2310/00131* (2013.01); *A61F 2310/00359* (2013.01)

(56) References Cited

U.S. PATENT DOCUMENTS

| | | | |
|---|---|---|---|
| 4,599,086 A | 7/1986 | Doty | |
| 4,743,256 A | 5/1988 | Brantigan | |
| 4,834,757 A | 5/1989 | Brantigan | |
| 4,904,261 A | 2/1990 | Dove et al. | |
| 4,917,704 A | 4/1990 | Frey | |
| 4,955,908 A | 9/1990 | Frey | |
| 5,002,576 A | 3/1991 | Fuhrmann et al. | |
| 5,364,399 A | 11/1994 | Lowery et al. | |
| 5,397,364 A | 3/1995 | Kozak et al. | |
| 5,458,641 A | 10/1995 | Jiminez | |
| 5,514,180 A | 5/1996 | Heggeness | |
| 5,549,612 A | 8/1996 | Yapp et al. | |
| 5,645,596 A | 7/1997 | Kim et al. | |
| 5,861,041 A | 1/1999 | Tienboon | |
| 5,888,223 A | 3/1999 | Bray, Jr. | |
| 6,045,579 A | 4/2000 | Hochshuler | |
| 6,066,175 A | 5/2000 | Henderson et al. | |
| 6,146,421 A | 11/2000 | Gordon | |
| 6,156,037 A | 12/2000 | LeHuec et al. | |
| 6,200,347 B1 | 3/2001 | Anderson et al. | |
| 6,206,922 B1 | 3/2001 | Zdeblick et al. | |
| 6,231,610 B1 | 5/2001 | Geisler | |
| 6,235,033 B1 | 5/2001 | Brace et al. | |
| 6,235,059 B1 | 5/2001 | Benezech | |
| 6,258,089 B1 | 7/2001 | Campbell et al. | |
| 6,342,074 B1 | 1/2002 | Simpson | |
| 6,364,880 B1 | 4/2002 | Michelson | |
| 6,383,186 B1 | 5/2002 | Michelson | |
| 6,425,920 B1 | 7/2002 | Hamada | |
| 6,432,106 B1 | 8/2002 | Fraser | |
| 6,468,311 B2 * | 10/2002 | Boyd | A61F 2/28 623/17.11 |
| 6,471,724 B2 | 10/2002 | Zdeblick | |
| 6,482,233 B1 | 11/2002 | Aebi | |
| 6,520,993 B2 | 2/2003 | James | |
| 6,540,785 B1 | 4/2003 | Gill et al. | |
| 6,558,387 B2 | 5/2003 | Errico | |
| 6,558,423 B1 | 5/2003 | Michelson | |
| 6,558,424 B2 | 5/2003 | Thalgott | |
| 6,562,073 B2 | 5/2003 | Foley | |
| 6,629,998 B1 | 10/2003 | Lin | |
| 6,666,889 B1 | 12/2003 | Commarmond | |
| 6,682,563 B2 | 1/2004 | Scharf | |
| 6,709,458 B2 | 3/2004 | Michelson | |
| 6,730,127 B2 | 5/2004 | Michelson | |
| 6,740,118 B2 | 5/2004 | Eisermann et al. | |
| 6,793,658 B2 | 9/2004 | Lehuec | |
| 6,805,714 B2 | 10/2004 | Sutcliffe | |
| 6,827,740 B1 | 12/2004 | Michelson | |
| 6,835,206 B2 | 12/2004 | Jackson | |
| 6,849,093 B2 | 2/2005 | Michelson | |
| 6,887,272 B2 | 5/2005 | Shinomiya | |
| 6,899,735 B2 | 5/2005 | Coates et al. | |
| 6,972,019 B2 | 12/2005 | Michelson | |
| 7,001,432 B2 | 2/2006 | Keller et al. | |
| 7,025,787 B2 | 4/2006 | Bryan et al. | |
| 7,044,972 B2 | 5/2006 | Mathys, Jr. | |
| 7,137,997 B2 | 11/2006 | Paul | |
| 7,147,665 B1 | 12/2006 | Bryan et al. | |
| 7,153,325 B2 | 12/2006 | Kim et al. | |
| 7,163,561 B2 | 1/2007 | Michelson | |
| 7,172,627 B2 | 2/2007 | Fiere et al. | |
| 7,192,447 B2 | 3/2007 | Rhoda | |
| 7,232,464 B2 | 6/2007 | Matthieu et al. | |
| 7,238,203 B2 | 7/2007 | Bagga et al. | |
| 7,276,082 B2 | 10/2007 | Zdeblick et al. | |
| 7,309,357 B2 | 12/2007 | Kim | |
| 7,320,708 B1 | 1/2008 | Bernstein | |
| 7,594,931 B2 | 9/2009 | Louis et al. | |
| 7,618,456 B2 | 11/2009 | Matthieu | |
| 7,771,475 B2 | 8/2010 | Michelson | |
| 7,794,502 B2 | 9/2010 | Michelson | |
| 7,846,207 B2 | 12/2010 | Lechmann | |
| 7,850,731 B2 | 12/2010 | Brittain | |
| 7,862,616 B2 | 1/2011 | Lechmann | |
| 7,875,076 B2 | 1/2011 | Matthieu | |
| 7,972,381 B2 | 7/2011 | Michelson | |
| 8,100,976 B2 | 1/2012 | Bray et al. | |
| 8,105,383 B2 | 1/2012 | Michelson | |
| 8,114,162 B1 | 2/2012 | Bradley | |
| 8,137,403 B2 | 3/2012 | Michelson | |
| 8,137,405 B2 | 3/2012 | Kostuik et al. | |
| 8,216,312 B2 | 7/2012 | Gray | |
| 8,268,000 B2 | 9/2012 | Waugh et al. | |
| 8,273,127 B2 * | 9/2012 | Jones | A61F 2/4455 623/17.16 |
| 8,323,343 B2 | 12/2012 | Michelson | |
| 8,328,872 B2 | 12/2012 | Duffield et al. | |
| 8,343,222 B2 | 1/2013 | Cope | |
| 8,425,607 B2 | 4/2013 | Waugh et al. | |
| 8,439,977 B2 | 5/2013 | Kostuik et al. | |
| 8,486,149 B2 * | 7/2013 | Saidha | A61F 2/4455 623/17.16 |
| 8,540,774 B2 | 9/2013 | Kueenzi et al. | |
| 9,149,365 B2 * | 10/2015 | Lawson | A61F 2/442 |
| 9,237,957 B2 * | 1/2016 | Klimek | A61F 2/30744 |
| 9,277,946 B2 * | 3/2016 | Hooper | A61B 17/8047 |
| 9,364,340 B2 * | 6/2016 | Lawson | A61F 2/4455 |
| 9,402,738 B2 * | 8/2016 | Niemiec | A61F 2/447 |
| 9,486,327 B2 * | 11/2016 | Martynova | A61F 2/447 |
| 9,526,630 B2 * | 12/2016 | Klimek | A61F 2/30744 |
| 9,545,320 B2 * | 1/2017 | Padovani | A61F 2/442 |
| 9,585,765 B2 * | 3/2017 | Niemiec | A61F 2/4455 |
| 9,968,461 B2 * | 5/2018 | Zappacosta | A61F 2/442 |
| 10,179,053 B2 * | 1/2019 | Zappacosta | A61F 2/442 |
| 10,925,750 B2 * | 2/2021 | Zappacosta | A61F 2/447 |
| 2001/0005796 A1 | 6/2001 | Zdeblick | |
| 2001/0034553 A1 | 10/2001 | Michelson | |
| 2002/0004683 A1 | 1/2002 | Michelson | |
| 2002/0010511 A1 | 1/2002 | Michelson | |
| 2002/0016595 A1 | 2/2002 | Michelson | |
| 2002/0082597 A1 | 6/2002 | Fraser | |
| 2002/0138146 A1 | 9/2002 | Jackson | |
| 2002/0143399 A1 | 10/2002 | Sutcliffe | |
| 2002/0147450 A1 | 10/2002 | Lehuec | |
| 2003/0045939 A1 | 3/2003 | Casutt | |
| 2003/0105528 A1 | 6/2003 | Shimp et al. | |

(56) References Cited

U.S. PATENT DOCUMENTS

| | | |
|---|---|---|
| 2003/0125739 A1 | 7/2003 | Bagga |
| 2003/0167091 A1 | 9/2003 | Scharf |
| 2003/0181981 A1 | 9/2003 | Lemaire |
| 2004/0078078 A1 | 4/2004 | Shepard |
| 2004/0082998 A1 | 4/2004 | Shinomiya |
| 2004/0082999 A1 | 4/2004 | Robert, Jr. |
| 2004/0117018 A1 | 6/2004 | Michelson |
| 2004/0143270 A1 | 7/2004 | Zucherman et al. |
| 2004/0143332 A1 | 7/2004 | Krueger et al. |
| 2004/0176853 A1 | 9/2004 | Sennett et al. |
| 2004/0199253 A1* | 10/2004 | Link ............... A61F 2/4425 623/17.11 |
| 2005/0055098 A1 | 3/2005 | Zdeblick et al. |
| 2005/0065607 A1 | 3/2005 | Gross |
| 2005/0149192 A1 | 7/2005 | Zucherman et al. |
| 2005/0149193 A1 | 7/2005 | Zucherman et al. |
| 2005/0159819 A1 | 7/2005 | McCormack et al. |
| 2005/0171607 A1 | 8/2005 | Michelson |
| 2005/0177236 A1 | 8/2005 | Mathieu et al. |
| 2005/0187625 A1 | 8/2005 | Wolek et al. |
| 2005/0240267 A1 | 10/2005 | Randall et al. |
| 2005/0240271 A1 | 10/2005 | Zubok et al. |
| 2005/0256574 A1 | 11/2005 | Paul et al. |
| 2006/0085071 A1 | 4/2006 | Lechmann et al. |
| 2006/0116767 A1 | 6/2006 | Magerl et al. |
| 2006/0129240 A1 | 6/2006 | Lessar et al. |
| 2006/0217809 A1 | 9/2006 | Albert et al. |
| 2007/0088441 A1 | 4/2007 | Duggal et al. |
| 2007/0106388 A1 | 5/2007 | Michelson |
| 2007/0123987 A1 | 5/2007 | Bernstein |
| 2007/0135923 A1 | 6/2007 | Peterman et al. |
| 2007/0162130 A1 | 7/2007 | Rashbaum et al. |
| 2007/0168032 A1 | 7/2007 | Muhanna et al. |
| 2007/0225806 A1 | 9/2007 | Squires et al. |
| 2007/0225810 A1 | 9/2007 | Colleran et al. |
| 2007/0225812 A1 | 9/2007 | Gill |
| 2007/0233253 A1 | 10/2007 | Bray et al. |
| 2007/0250167 A1 | 10/2007 | Bray |
| 2007/0270961 A1 | 11/2007 | Ferguson |
| 2008/0046083 A1 | 2/2008 | Hewko |
| 2008/0051890 A1 | 2/2008 | Waugh et al. |
| 2008/0051907 A1 | 2/2008 | Marik |
| 2008/0133013 A1 | 6/2008 | Duggal et al. |
| 2008/0281425 A1* | 11/2008 | Thalgott ............... A61F 2/447 623/17.16 |
| 2008/0306596 A1* | 12/2008 | Jones ............... A61B 17/8042 623/17.16 |
| 2009/0076608 A1 | 3/2009 | Gordon et al. |
| 2009/0210062 A1 | 8/2009 | Thalgott et al. |
| 2010/0057206 A1* | 3/2010 | Duffield ............... A61F 2/30771 623/17.16 |
| 2010/0087925 A1 | 4/2010 | Kostuik et al. |
| 2010/0145460 A1 | 6/2010 | McDonough |
| 2010/0312345 A1* | 12/2010 | Duffield ............... A61F 2/4465 623/17.16 |
| 2010/0312346 A1* | 12/2010 | Kueenzi ............... A61F 2/44 623/17.16 |
| 2011/0087327 A1 | 4/2011 | Lechmann |
| 2011/0166658 A1 | 7/2011 | Garber et al. |
| 2011/0251689 A1 | 10/2011 | Seifert et al. |
| 2012/0078371 A1 | 3/2012 | Gamache et al. |
| 2012/0078373 A1 | 3/2012 | Gamache et al. |
| 2012/0179259 A1* | 7/2012 | McDonough ......... A61F 2/4455 623/17.16 |
| 2012/0245690 A1 | 9/2012 | Cowan, Jr. et al. |
| 2012/0290089 A1 | 11/2012 | Melamed |
| 2013/0110247 A1 | 5/2013 | Doran et al. |
| 2014/0012380 A1 | 1/2014 | Laurence et al. |
| 2014/0039623 A1* | 2/2014 | Iott ............... A61F 2/4455 623/17.16 |
| 2014/0180422 A1* | 6/2014 | Klimek ............... A61F 2/30744 623/17.16 |
| 2014/0228957 A1* | 8/2014 | Niemiec ............ A61B 17/8605 623/17.16 |
| 2014/0228958 A1* | 8/2014 | Niemiec ............ A61F 2/30767 623/17.16 |
| 2014/0228959 A1* | 8/2014 | Niemiec ............... A61F 2/447 623/17.16 |
| 2014/0243981 A1* | 8/2014 | Davenport ............ A61F 2/4455 623/17.16 |
| 2014/0257487 A1* | 9/2014 | Lawson ............ A61B 17/8042 623/17.16 |
| 2014/0277487 A1* | 9/2014 | Davenport ............... A61F 2/447 623/17.16 |
| 2014/0277488 A1* | 9/2014 | Davenport ............... A61F 2/442 623/17.16 |
| 2014/0277489 A1* | 9/2014 | Davenport ............... A61F 2/447 623/17.16 |
| 2014/0277497 A1* | 9/2014 | Bennett ............... A61F 2/4465 623/17.16 |
| 2015/0190241 A1 | 7/2015 | Gowan |
| 2015/0328007 A1* | 11/2015 | Padovani ............... A61F 2/447 623/17.13 |
| 2015/0328009 A1* | 11/2015 | Zappacosta ............ A61F 2/4455 623/17.16 |
| 2015/0328010 A1* | 11/2015 | Martynova ............ A61F 2/442 623/17.16 |
| 2016/0089246 A1* | 3/2016 | Klimek ............ A61B 17/8042 623/17.16 |
| 2016/0095714 A1* | 4/2016 | Spangler ............... C08L 71/00 623/17.16 |
| 2017/0014241 A1* | 1/2017 | Martynova ............ A61F 2/442 |
| 2017/0049579 A1* | 2/2017 | Quinlan ............... A61F 2/447 |
| 2018/0235772 A1* | 8/2018 | Zappacosta ............ A61F 2/442 |
| 2019/0105175 A1* | 4/2019 | Zappacosta ............ A61F 2/4455 |
| 2019/0336304 A1* | 11/2019 | Burkhardt ............... A61F 2/447 |

FOREIGN PATENT DOCUMENTS

| | | |
|---|---|---|
| JP | 2013-540503 A | 11/2013 |
| JP | 2016512110 A | 4/2016 |
| JP | 2017501835 A | 1/2017 |
| WO | 1997023175 A1 | 7/1997 |
| WO | 1999063914 A1 | 12/1999 |
| WO | 2005007040 A1 | 1/2005 |
| WO | 2007098288 A2 | 8/2007 |
| WO | 2008014258 A2 | 1/2008 |
| WO | 2012115631 A1 | 8/2012 |
| WO | 2014138311 A1 | 9/2014 |

OTHER PUBLICATIONS

U.S. Appl. No. 60/777,732, filed Feb. 27, 2006, Messerli et al.
U.S. Appl. No. 60/838,229, filed Aug. 16, 2006, Hunziker et al.
Guidance Document: Intervertebral Body Fusion Device, U.S. Dept. of Health and Human Services, Food and Drug Administration (Jun. 12, 2007).
M. Spruit et al., The in vitro stabilizing effect of polyetheretherketone cages versus a titanium cage of similar design for anterior lumbar interbody fusion, 14(8) Eur. Spine J. 752, 752-758 (2005).
P. Schleicher et al., Biomechanical comparison of two different concepts for stand alone anterior lumbar interbody fusion, 17(12) Eur. Spine J. 1757, 1757-1765 (2008).
P.W. Pavlov et al., Anterior lumbar interbody fusion with threaded fusion cages and autologous bone grafts, 9 Eur. Spine J. 224, 224-229 (2000).
Synthes' SynFix Technique Guide device ("SynFix Technique Guide").

* cited by examiner

LATERALLY INSERTABLE INTERVERTEBRAL SPINAL IMPLANT

CROSS-REFERENCE TO RELATED APPLICATIONS

This patent application is a continuation-in-part of U.S. patent application Ser. No. 16/205,892, filed on Nov. 30, 2018, which is a continuation application of U.S. patent application Ser. No. 15/954,655 filed on Apr. 17, 2018 which is a divisional of U.S. patent application Ser. No. 14/509, 634, filed Oct. 8, 2014, which is a continuation-in-part of U.S. patent application Ser. No. 14/278,898 filed on May 15, 2014, the entire disclosures of which are incorporated herein by reference in their entireties for all purposes.

FIELD

The present disclosure generally relates to fixation devices and systems for positioning and immobilizing at least two adjacent vertebrae and methods related to the same. In particular, the present disclosure relates to interbody fusion devices with angled fixation holes configured to facilitate lateral arterial implantation.

BACKGROUND

The spine is the axis of the skeleton on which all of the body parts "hang". In humans, the normal spine has seven cervical, twelve thoracic and five lumbar segments. The lumbar spine situs upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The central of adjacent vertebrae are supported by intervertebral discs. The spinal disc and/or vertebral bodies may be displaced or damaged due to trauma, disease, degenerative defects, or wear over an extended period of time. One result of this displacement or damage to a spinal disc or vertebral body may be chronic back pain. In many cases, to alleviate back pain from degenerated of herniated discs, the disc is removed along with all or part of at least one neighboring vertebrae and is replaced by an implant that promotes fusion of the remaining bony anatomy.

Although most spinal surgeries are performed using a posterior (back) approach, in some cases a surgeon may choose an anterior (ALIF) approach for various reasons, for example, to allow more direct access to the intervertebral disk; to have the ability to add more lordosis (swayback) to the d spine; and to provide access to the spine without moving the nerves. Treatment of the disc at the L5/S1 level is particularly suitable for the ALIF approach due to the efficient vascular access below with bifurcation of the aorta and inferior vena cava. However, the ALIF approach typically requires organs and blood vessels be moved to the side. As such, in many cases, a vascular surgeon assists the orthopaedic surgeon with opening and exposing the disk space.

Additionally, the ALIF approach is typically performed with the patient in a supine position. As such, other procedures, for example, attaching a plate or rod to posterior spine, will generally require changing the position of the patient to provide posterior axis. The result is often increased surgical time and reduced surgical workflow.

SUMMARY

To meet this and other needs, an intervertebral implant has an overall footprint that matches that of a standard integrated-fixation ALIF, however, the means of attachment to the device and the angle at which the fixation is delivered, sit at an angle relative to the disc space.

According to at least one embodiment of the disclosure, an insertion tool and intervertebral implant kit is disclosed. The implant includes a body having a front end, a rear end and a pair of spaced apart first and second side walls extending between the front and rear ends. The front and rear ends extend in a transverse direction and a central axis of the body extends from the rear end to the front end. The rear end defines a first fastener hole having a first central axis and a second fastener hole having a second central axis. The first and second central axes extend parallel to one another at an acute angle relative to the body central axis in the transverse direction. The insertion tool includes a tool body extending from a proximal end to distal end. The distal end defines a face and the tool body defines at least two fastener passages with respective third and fourth central axes. The insertion tool is configured to support the implant such that the implant rear end extends along the face and the third and fourth central axes align with and are parallel to the first and second central axes, respectively, in the transverse direction.

According to at least one embodiment of the disclosure, a retraction assembly is disclosed. The retraction assembly includes a mounting plate with at least one mount extending therefrom. The mounting plate has a chamber extending therein with an adjustment screw extending into the chamber. A lateral adjustment arm has a first end with a shaft which is positioned in the chamber and engages the adjustment screw such that rotation thereof causes the lateral adjustment arm to move laterally relative to the mounting plate. The second end of the lateral adjustment arm defines a pivot mount. A pivot member is pivotally connected to the lateral adjustment arm at the pivot mount with a second adjustment screw extending from the lateral adjustment arm and engaging the pivot member such that rotation thereof causes pivoting of the pivot member relative to the lateral adjustment arm. A retraction blade connected to the pivot member.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION

Figure 1:
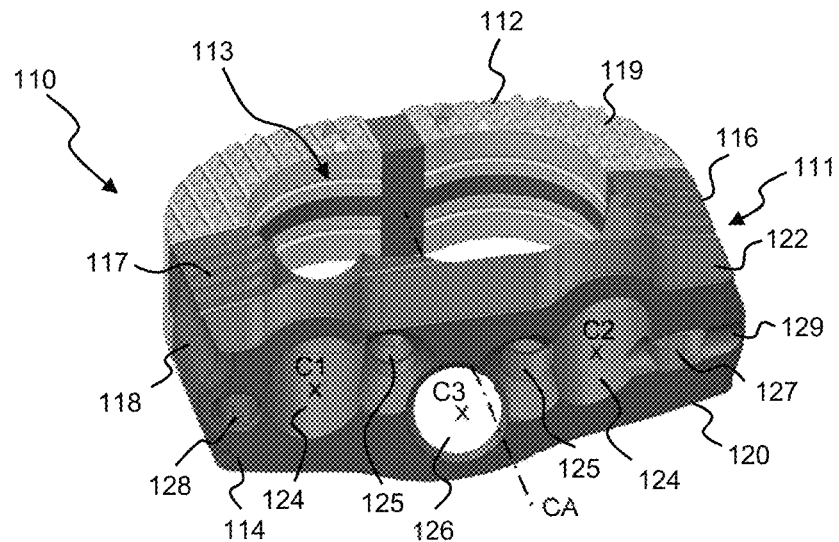
FIG. 1 is a bottom perspective view of an intervertebral implant according to an embodiment of the disclosure.
Figure 2:
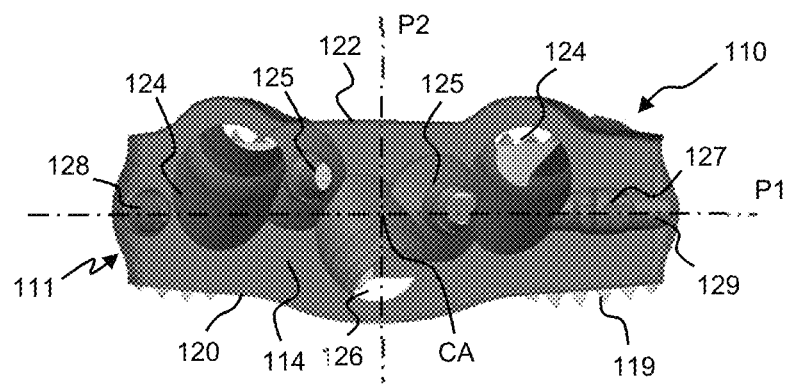
FIG. 2 is anterior elevation view of the intervertebral implant of FIG. 1.

Embodiments of the disclosure are generally directed to intervertebral implants, systems, and method of use thereof.

Referring to FIGS. 1-7, an embodiment of a lateral anterior lumbar interbody fusion implant 110 in accordance with an embodiment of the disclosure will be described. As illustrated, the implant 110 has a body 111 with a generally D-shaped configuration. The body 111 is defined by a posterior end 112, an anterior end 114 and side walls 116 and 118 extending therebetween. A hollow interior chamber 113 is defined within an inner perimeter of the body 111. The hollow interior chamber 113 is configured to receive bone growth promoting materials. The implant 110 has an upper surface 120 and a substantially parallel lower surface 122. It is noted that in FIGS. 1-4, the implant 110 is illustrated in an inverted position such that the lower or superior surface 122 is facing upward. The upper and lower surfaces 120, 122 define a plurality of serrations 117 along the side walls 116, 118 and a plurality of serrations 119 along the posterior end 112.

While the implant 110 is illustrated and described with a body 111 having a specific configuration, the disclosure is not limited to such. The body 111 may have various other configurations suitable for the disc space into which the implant 110 is intended. For example, the posterior end 112 may be formed with a taper or the implant 110 may have a wedge shape such that the entire body 111 tapers from the anterior end 114 to the posterior end 112. Similarly, the side walls 116, 118 may be angled toward one another rather than extending substantially parallel to one another. As yet another example, the body 111 may have an adjustable configuration. In each case, the implant body 111 will have a central axis CA extending from the anterior end 114 to the superior end 112. The central axis CA is located at the junction between the mid transverse plane P1 and the mid sagittal plane P2 and extends in each of the planes P1, P2 (see FIG. 2).

The anterior end 114 of the implant 110 includes a plurality of fastener holes 124, 126 through which anchors 140 or screws 150 (see FIGS. 4 and 6) extend to anchor the implant onto the vertebral body. Each of the fastener holes 124, 126 has a central axis C1, C2, C3. As is known in the art, the axes C1, C2, C3 may be angled superiorly or inferiorly relative to the transverse plane P1 such that the fasteners will be directed toward the superior or inferior vertebral body. In the illustrated embodiment, the axes C1, C2 of fastener holes 124 each extend inferiorly relative to the transverse plane P1 and the axis C3 of the fastener hole 126 extends superiorly relative to the transverse plane P1. Such configuration is not required and the implant may have other configurations with more or fewer holes and with different numbers of holes extending superiorly or inferiorly. Additionally, when utilizing anchors 140 such angling may not be as necessary or necessary at all since the curved configuration of the anchor blade body 142 is curved and will naturally extend superiorly or inferiorly.

Figure 5:
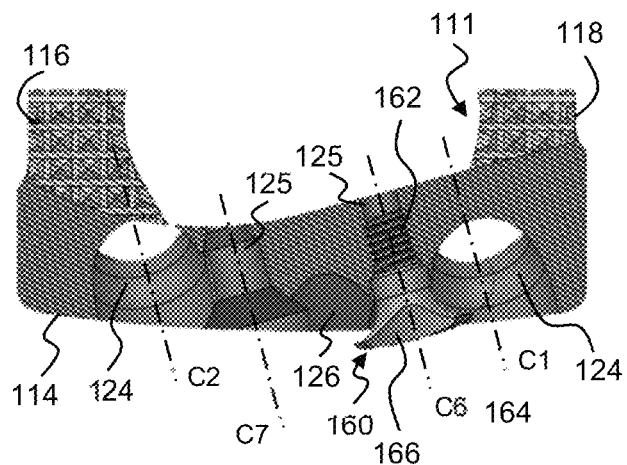
FIG. 5 is a cross-sectional view of the anterior portion of the implant of FIG. 1 with a locking screw positioned therein.

Secondary holes 125 are provided to receive respective blocking set screws 160 (see FIG. 5). The secondary holes 125 each extend along a central axis C6, C7. Each of the secondary hole axes C6, C7 is generally parallel to the transverse plane P1. A blind hole 127 with a slot 129 and a threaded hole 128 are provided for receiving an instrument 170 that is used for inserting the implant 110, as will be described hereinafter. The central axis C4 of the blind hole 127 and the central axis C5 of the threaded hole 128 also are generally parallel to the transverse plane P1.

Figure 3:
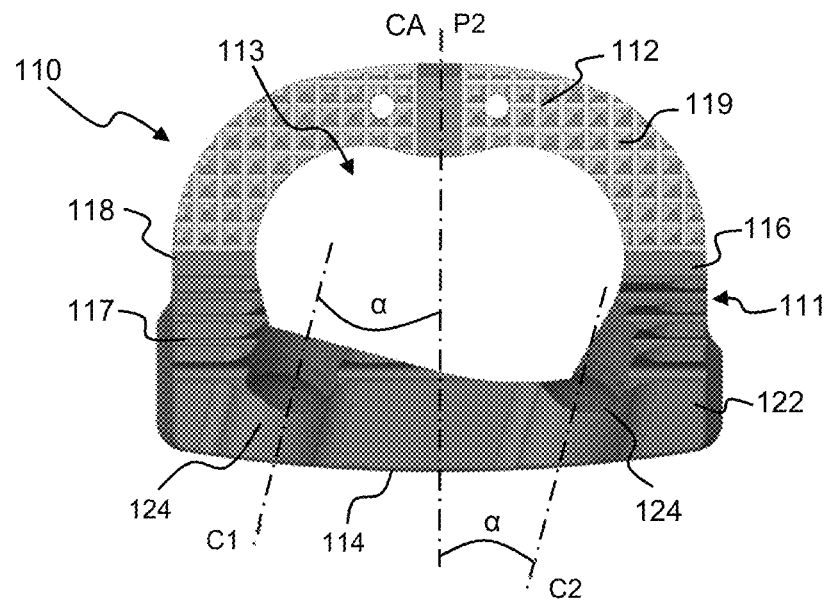
FIG. 3 is bottom plan view of the intervertebral implant of FIG. 1.
Figure 6:
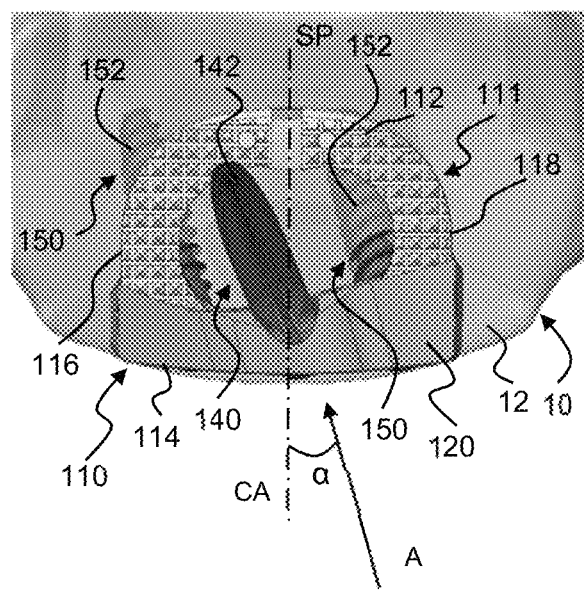
FIG. 6 is a top plan view of the intervertebral implant of FIG. 1 positioned relative to a vertebra.

In addition to the angular orientation in the superior/inferior direction, each of the axes C1-C7 is also angled relative to the sagittal plane P2 (and thereby the central axis CA) in the transverse direction to facilitate lateral insertion of the implant 110. Referring to FIG. 3, the axes C1 and C2 are parallel to one another and each are angled relative the sagittal plane P2 at an acute angle α. While not shown in FIG. 3, the axis C3 of fastener hole 126 will also be angled relative the sagittal plane P2 at the acute angle α and will be parallel to the axes C1 and C2. As seen in FIG. 6, upon fixation of the implant 110 relative to the vertebral body 12 of the spine 10, the shaft 142, 152 of each of the fasteners 140, 150 will parallel to each other in the transverse direction, each extending at the angle aα relative to the central axis CA of the implant 110.

Figure 7:
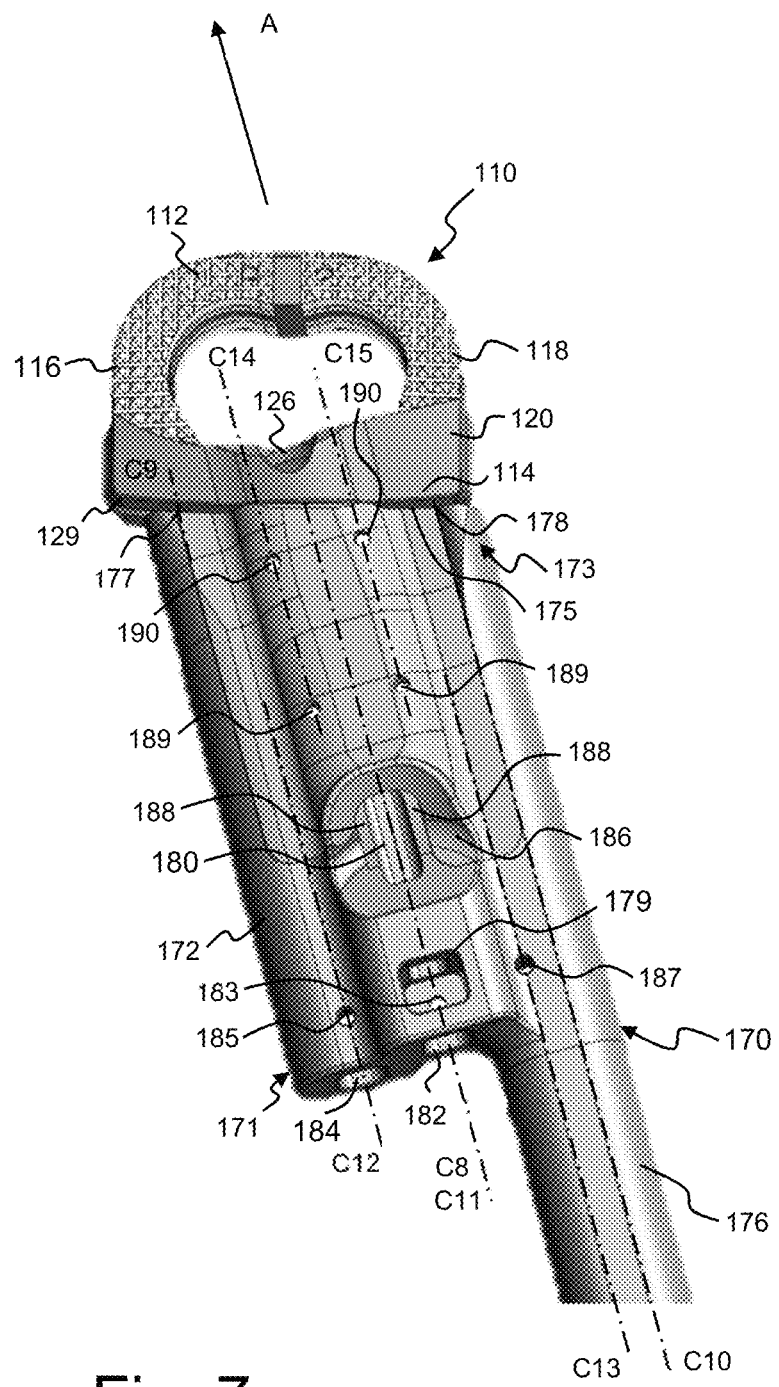
FIG. 7 is a perspective view illustrating the intervertebral implant of FIG. 1 connected to an insertion tool in accordance with an embodiment of the disclosure.

The angle α is chosen to approximate the angle of the lateral insertion path A of the implant relative to the sagittal plane SP of the vertebral body 12 of the spine 10 as shown in FIG. 6. As shown in FIG. 7, such allows the insertion tool 170 to hold the implant for insertion along the path A and also allows the fasteners 140, 150 to be delivered along the same path along which the insertion tool will extend. Upon proper positioning, the central axis CA of the implant 110 will extend approximately along the sagittal plane SP of the vertebral body 12 and the fasteners 140, 150 may be easily directed into engagement with the superior and inferior vertebral bodies.

Figure 4:
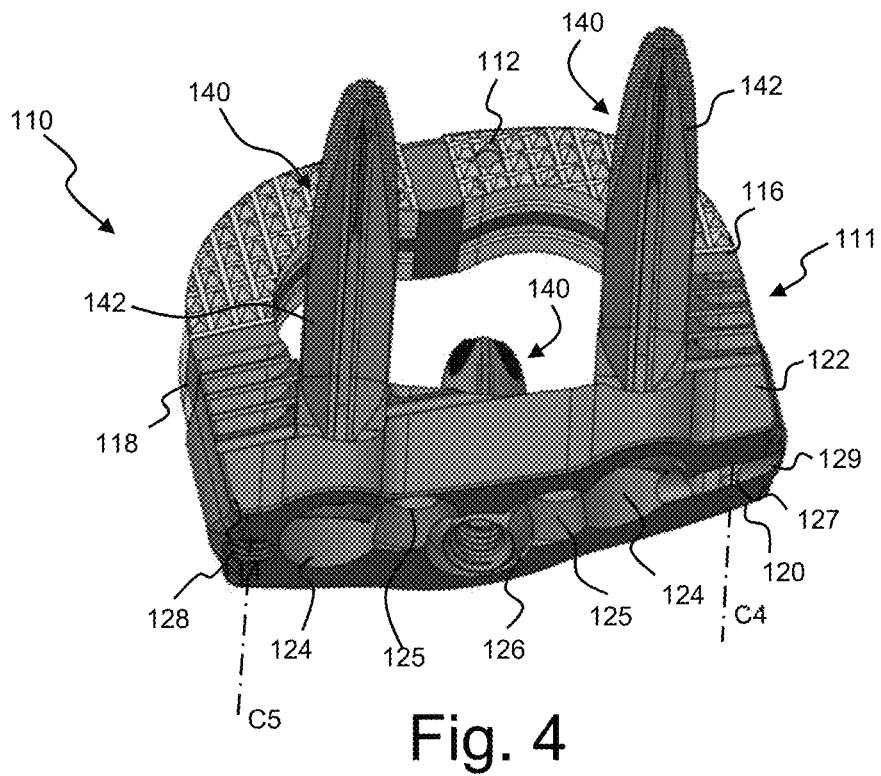
FIG. 4 is a perspective view similar to FIG. 1 illustrating fasteners positioned within the implant.

Referring to FIG. 4, to facilitate easy mounting of the insertion tool 170 relative to implant 110, the axis C4 of the blind hole 127 and the axis C5 of the threaded hole 128 also extend parallel to the fastener hole axes C1-C3. As such, the insertion tool 170 may be delivered to the implant 110 along the path A and then a threaded connector (not shown) can be advanced parallel to the axis of the tool 170.

Referring to FIG. 5, to facilitate easy engagement of the blocking set screws 160, the axes C6, C7 of the secondary holes 125 also preferably extend parallel to the fastener hole axes C1-C3. With the shaft 162 of each blocking set screw 160 extending into a respective secondary hole 125, the head 164 thereof will be co-axial with the secondary hole 125. As such, a driver (not shown) may be moved along at the same angle defined by the insertion tool 170 to engage the head 164 and move the set screw 160 from a non-blocking position, wherein the recess(es) 166 on the head 164 are aligned with a respective fastener hole 124, 126, to a blocking position wherein the head 164 overlies the fastener holes 124, 126.

Having generally described the implant 110, the insertion tool 170 and implant procedure will be described in more detail with reference to FIG. 7. The insertion tool 170 includes a main body 172 extending from a proximal end 171 to a distal end 173 along a tool central axis C8. The distal end 173 defines a face 175 configured to engage the anterior end 114 of the implant 110. The face 175 is angled relative to the tool central axis C8 such that upon mounting of the implant 110 on the tool 170, the tool central axis C8 will be parallel with the central axes C1-C7 of the implant in the transverse direction. The tool body 172 may define one or more openings 179 configured to mount other tools thereto, for example, an articulating table arm or a pushing handle (not shown).

To connect the insertion tool 170 to the implant 110, a pin (not shown) extends from the tool face 175 at the location labeled 177 which aligns with the blind hole 127 of the implant. The pin extends along an axis C9 which is parallel to the tool central axis C8 such that the pin will extend into the blind hole 127 and the face 175 will extend along the anterior end 114 of the implant 110. A threaded connector (not shown) extends through a passage in the insertion tool 170 such that the threaded connector extends from the face 175 at the location labeled 178 which aligns with the threaded hole 128. The tool 170 may include a handle portion 176 through which the connector passage extends. The threaded connector passage extends along an axis C10 that is parallel with the tool central axis C8 such that the threaded connector can be advanced into and threadably engage the threaded hole 128, thereby mounting the implant 110 to the face 175 of the insertion tool 170.

The tool body 172 defines fastener passages 182, 184 (only two shown in FIG. 7) configured to align with each of the fastener holes 124, 126. The axes C11, C12, C13 of the fastener passages 182, 184 extend parallel to the tool central axis C8. As such, the fasteners 140, 150 may be easily passed through the insertion tool 170 into the respective fastener hole 124, 126. In the event a curved anchor blade 142 is utilized, the passages 182, 184 may have corresponding curves (in the superior/inferior direction). An alignment hole 183, 185, 187 extends into each of the fastener passages 182, 184.

To access the blocking set screws 160, an opening 186 extends into the body 172 to set screw passages 188 on either side of the tube 180 defining the fastener passage 182. Each set screw passage 188 aligns with a respective secondary hole 125. The axes C14, C15 of the set screw passages 188 extend parallel to the tool central axis C8. As such, a drive tool (not shown) may be passed through each set screw passage 188 to engage and rotate a respective set screw 160. Alignment holes 189, 190 extend into each of the set screw passages 188.

While the illustrated embodiments have a fixed angle $\alpha$ for the holes and tool passages, it is possible to make the angle adjustable such that the implant 110 may be adjustable for different anatomies. For example, each of the implant holes could include a ball and socket configuration which is lockable at a desired angle. The face of the insertion tool could be pivotably adjustable to match the angle set for the implant holes. Other means for adjusting the angle of the holes and the tool passages may also be utilized.

The implant 110 and insertion tool 170 provide greater ease of use off-axis to disc spaces, for example, the L5-S1 disc space. Traditional ALIF implants require a straight-on approach, which is made more difficult when the patient is positioned on their side. The angled approach to the disc space with the angled tool, paired with a matching angle by which the fixation is delivered and blocked in place facilitates operating on the L5-S1 disc space, or other desired disc spaces, via a lateral position, or "lateral ALIF".

Such lateral ALIF requires retraction of different anatomy to access the disc space with a patient on their side. Referring to FIGS. 8-14, a retraction assembly 220 which offers increased ability to adjust blade position as well as specific options for retracting the anatomy as it pertains to accessing the disc space with a patient on their side will be described.

Figure 8:
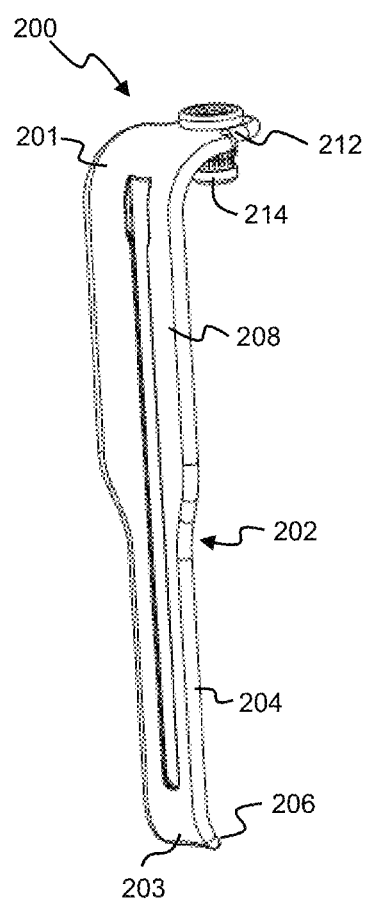
FIGS. 8-10 are perspective, side and elevation views, respectively, of a retraction blade in accordance with an embodiment of the disclosure.
Figure 9:
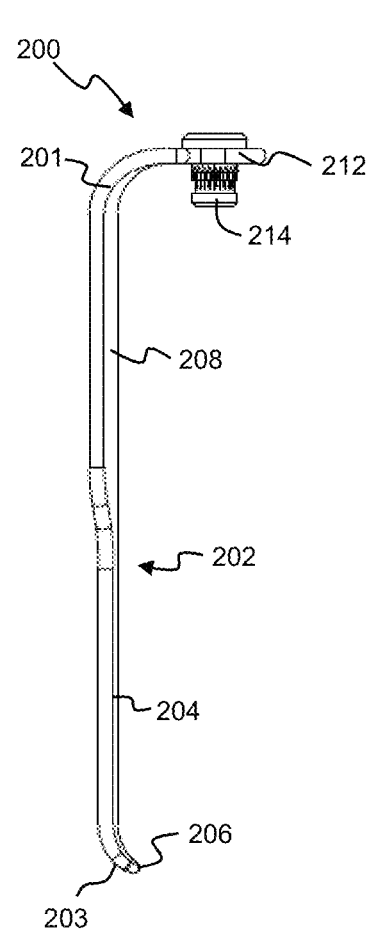
Figure 10:
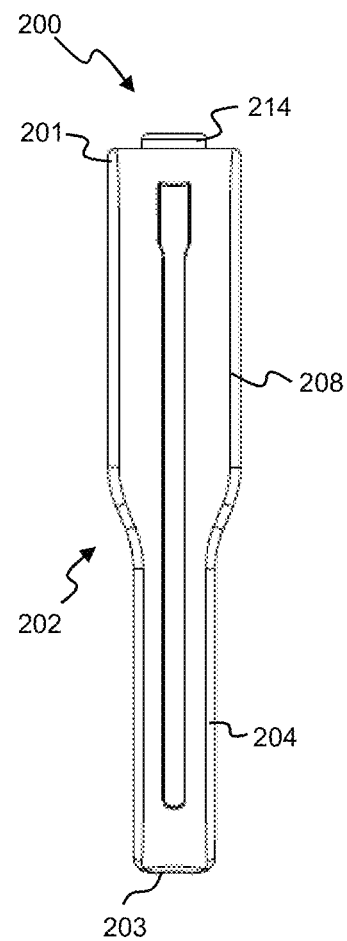

Referring to FIGS. 8-10, an illustrative blade 200 for use with the retraction assembly 220 illustrated in FIG. 14 will be described. The blade 200 includes a body 202 extending from a proximal end 201 to a distal end 203. The distal end 203 of the body 202 includes a portion 204 having a narrower width than the portion 208 at the proximal end 201. The body 202 may have a lateral curvature as illustrated. Additionally, a curved tip 206 is defined at the distal end 203 of the body 202. The curved tip 206 may also narrow as it moves distally. The narrow portion 204 and the curved tip 206 allow for retraction of vasculature, for example, at the crotch of the bifurcation. The wider portion 208 at the proximal end 201 provides better retraction of soft tissue. The bi-functionality of the blade 200 serves well for a minimally invasive anterior approach where the vessels need to be mobilized. A flange portion 212 extends from the proximal end 201 and supports a connecting member 214 configured to engage and mount to a pivoting member 250 of the retraction assembly 220 as will be described hereinafter.

Figure 11:
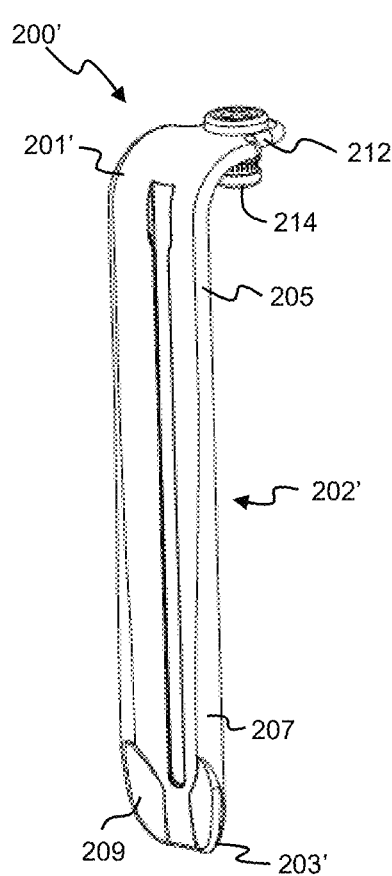
FIGS. 11-13 are perspective, side and elevation views, respectively, of a retraction blade in accordance with another embodiment of the disclosure.
Figure 12:
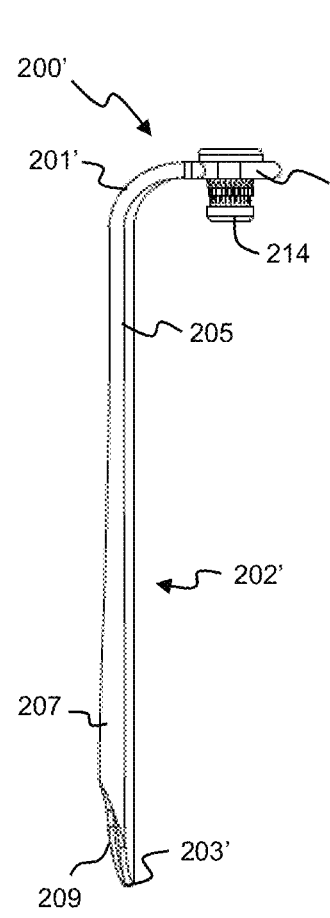
Figure 13:
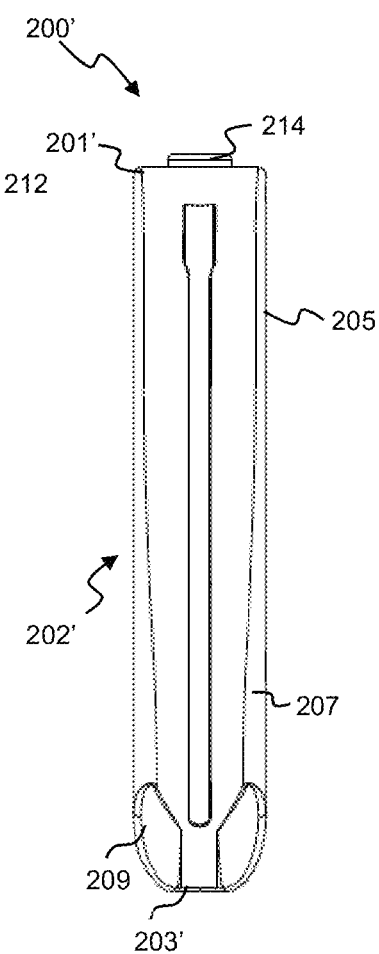

Referring to FIGS. 11-13, another illustrative blade 200' for use with the retraction assembly 220 illustrated in FIG. 14 will be described. The blade 200' includes a body 202' extending from a proximal end 201' to a distal end 203'. The body 202' tapers in thickness from a thinner portion 205 at the proximal end 201' to a thicker portion at the distal end 203'. This configuration serves to stiffen the blade 200'. Again, the body 202' may have a lateral curvature as illustrated. Additionally, a scalloped tip 209 is defined at the distal end 203' of the body 202'. The scalloped tip 209 may be used to sit under bony anatomy and act as a lever for retracting soft tissue. Again, a flange portion 212 extends from the proximal end 201' and supports a connecting member 214 configured to engage and mount to a pivoting member 250 of the retraction assembly 220.

Figure 14:
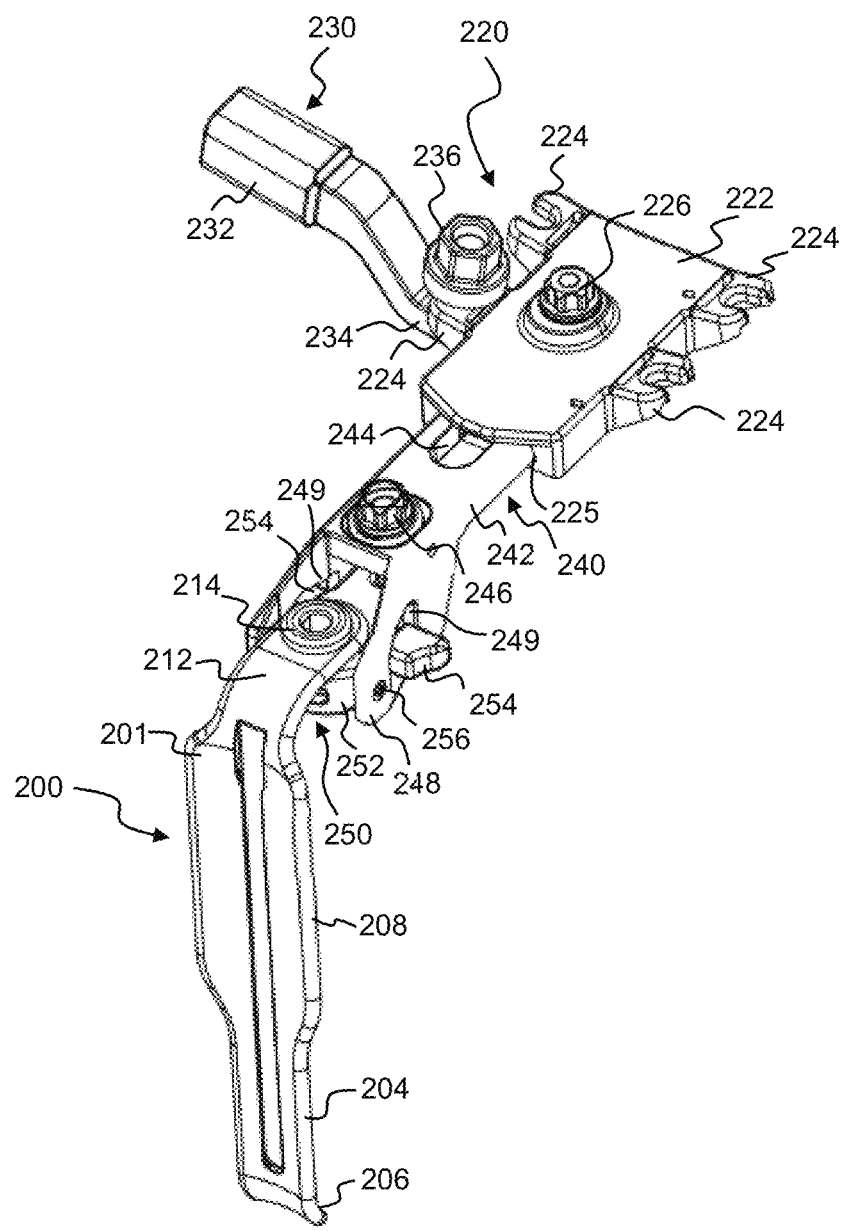
FIG. 14 is a perspective view of the retraction blade of FIGS. 8-10 positioned in a mounting system in accordance with an embodiment of the disclosure.

Referring to FIG. 14, a retraction assembly 220 in accordance with an embodiment of the disclosure will be described. The retraction assembly 220 includes a mounting plate 222 with one or more mounts 224 extending therefrom. The mounts 224 are configured for mounting directly to an articulating table arm 230 or other structure, for example, mounting to extensions which mount to a more traditional ring-based design. In the illustrated embodiment, the table arm 230 includes an arm 232 which terminates in a screw platform 234 supporting a connecting screw 236. The connecting screw 236 is positioned within the mount 224 and tightened such that the mount 234 is secured between the head of the screw 236 and the screw platform 234 to secure the mounting plate 222.

A cavity 225 extends into the mounting plate 222 and is configured to receive a shaft 242 of a lateral adjustment arm 240. The shaft 242 defines a slot 244 into which an adjustment screw 226 of the mounting plate 222 extends. The screw 226 engages within the slot 244 and thereby defines the range of later movement of the lateral adjustment arm 240. The screw 226 and slot 244 may have various adjustment configurations, for example, a friction lock, gear assembly, or a rack and pinion arrangement.

The opposite end of the lateral adjustment arm 240 defines a fork 248 with a pair of openings 249 on each side to support a pivot member 250. The pivot member 250 includes a body 252 with an opening configured to receive the blade connecting member 214 to mount the blade 200 on the assembly 220. A pivot pin 256 extends through the fork 248 and end of the pivot member body 250 such that the pivot member 250 is pivotally supported relative to the fork 248. A pair of opposed extensions 254 extend into the openings 249 and define the range of pivot. An adjustment screw 246 on the lateral adjustment arm 240 engages an opposite end of the pivot member 250 such that rotation thereof causes the pivot member 250, and thereby the blade 200, to pivot. Pivoting of the blade 200 allows the blade 200 to change angulation to compensate for various anatomy and tissue.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. An insertion tool and intervertebral implant kit, the kit comprising:
    an implant comprising: an implant body having a front end, a rear end and a pair of spaced apart first and second side walls extending between the front and rear ends with the front and rear ends extending in a transverse direction and a central axis of the implant body extending from the rear end to the front end, wherein the rear end defines a first fastener hole having a first central axis and a second fastener hole having a second central axis, the first and second central axes extending parallel to one another at an acute angle relative to the implant body central axis in the transverse direction; and
    an insertion tool comprising: a tool body extending from a proximal end to distal end, the distal end defining a face and the tool body defining at least two fastener passages with respective third and fourth central axes, wherein the insertion tool is configured to support the implant such that the implant rear end extends along the face and the third and fourth central axes align with and are parallel to the first and second central axes, respectively, in the transverse direction.

2. The kit of claim 1, wherein the implant rear end defines a third fastener hole having a fifth central axis which is parallel to the first and second axes in the transverse direction and the insertion tool body defines a third fastener passage having a sixth central axis which aligns with and is parallel to the fifth central axis in the transverse direction when the implant is supported on the insertion tool.

3. The kit of claim 1, wherein the first central axis extends in a first direction relative to a superior/inferior direction and the second central axis extends in a second opposite direction relative to the superior/inferior direction.

4. The kit of claim 1, wherein at least one blocking set screw hole is defined by the implant rear end adjacent at least one of the fastener holes, the blocking set screw hole having a seventh central axis which is parallel to the first and second axes in the transverse direction and the insertion tool body defines a driver passage having an eigth central axis which aligns with and is parallel to the seventh central axis in the transverse direction when the implant is supported on the insertion tool.

5. The kit claim 4, further comprising a blocking set screw positioned within the blocking set screw hole and moveable between a non-blocking position and a blocking position by a driver positioned within the driver passage.

6. The kit of claim 1, wherein at least one insertion tool receiving hole is defined by the rear end and has a ninth central axis which is parallel to the first and second axes in the transverse direction and a mounting element extends from the face of the insertion tool body and is configured to be received in the insertion tool receiving hole.

7. The kit of claim 1, further comprising a fastener positioned in each fastener hole, each of the fasteners including a shaft and the shafts are parallel to one another in the transverse direction.

\* \* \* \* \*